United States Patent [19]

Eller et al.

[11] Patent Number: 4,652,681
[45] Date of Patent: Mar. 24, 1987

[54] AMINOALKOXY DERIVATIVES OF PROPRANOLOL FOR IMMUNOASSAY APPLICATIONS

[75] Inventors: Thomas D. Eller, Mount Pleasant; Daniel R. Knapp, Charleston, both of S.C.

[73] Assignee: Drug Science Foundation, Charleston, S.C.

[21] Appl. No.: 368,672

[22] Filed: Apr. 15, 1982

[51] Int. Cl.$^4$ .............................................. C07C 93/06
[52] U.S. Cl. ................................ 564/349; 260/501.18; 562/451; 562/467; 424/85; 436/545
[58] Field of Search ................ 562/451, 467; 564/345; 260/501.8

[56] References Cited

U.S. PATENT DOCUMENTS

| | | | |
|---|---|---|---|
| 2,129,674 | 9/1938 | Christiansen et al. | 564/353 X |
| 3,322,758 | 5/1967 | Thiele et al. | 564/353 X |
| 3,432,545 | 3/1969 | Howe | 564/349 X |
| 3,519,675 | 7/1970 | Lednicer | 562/451 X |
| 3,678,117 | 7/1972 | Middleton | 564/353 X |
| 3,683,009 | 8/1972 | Middleton | 564/353 X |
| 3,712,929 | 1/1973 | Middleton | 564/353 X |
| 3,878,187 | 4/1975 | Schneider et al. | 562/451 X |
| 3,994,902 | 11/1976 | Bell | 564/353 X |
| 4,092,479 | 5/1978 | Parson, Jr. et al. | 548/312 |
| 4,094,908 | 6/1978 | Toth et al. | 564/327 X |
| 4,241,177 | 12/1980 | Singh et al. | 564/349 X |
| 4,311,685 | 1/1982 | Snyder | 424/1 |
| 4,329,502 | 5/1982 | Singh et al. | 564/349 |
| 4,338,333 | 7/1982 | Ainsworth et al. | 562/451 X |

OTHER PUBLICATIONS

Nickerson, et al., Drugs Inhibiting Adrenergic Nerves and Structures Inervated by Them, *The Pharmacological Basis of Therapeutics*, 5th Ed., (1977) Chap. 26.

Primary Examiner—Robert V. Hines
Attorney, Agent, or Firm—Pahl, Lorusso & Loud

[57] ABSTRACT

Derivatives of propranolol which have the following structure:

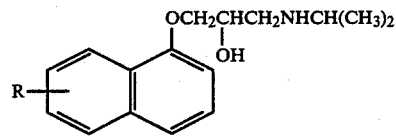

where R is X—$(CH_2)_n$—O, X is $NH_2$ or COOH, n is 1,2,3,4, or 5, provided that when n is 1, X must be COOH, and R is attached in the 4', 5', 6', 7' or 8' position. The compounds are useful in immunoassay applications to (1) conjugate to a protein carrier in order to prepare antibodies to propranolol and (2) to conjugate to a tracer moiety such as a radiolabeled ligand, an enzyme, an enzyme substrate or a fluorescent dye.

2 Claims, 3 Drawing Figures

AMINOALKOXY DERIVATIVES OF PROPRANOLOL FOR IMMUNOASSAY APPLICATIONS

This invention was made with Government support under grants GM 20387 and RR 01239 awarded by the National Institutes of Health. The Government has certain rights in this invention.

BACKGROUND OF THE INVENTION

The invention relates to an immunoassay of propranolol and more particularly to new chemical compounds which are derivatives of propranolol and which are useful in immunoassay applications.

Propranolol is among the most widely prescribed prescription drugs in the world and is also the subject of extensive research worldwide. Propranolol is a beta-adrenergic receptor blocking drug. It specifically competes with beta-adrenergic receptor stimulants for available beta receptor sites.

Propranolol is prescribed primarily for the treatment of hypertension, angina pectoris and arrhythmia. The objective of propranolol therapy is to decrease adverse sympathetic stimulation, but not to the degree that may impair necessary sympathetic support and possibly precipitate heart failure.

One of the major problems involved in prescribing propranolol is determining the proper dosage requirement for a patient. While the desirable concentration of propranolol in the patient's blood is known, it has been found that the uptake of this drug by most patients is variable, so that one has no assurance that a particular dose of propranolol administered to the patient will produce the desired concentration in the blood. Attaining the optimal dose is important in achieving maximal therapeutic benefit and in avoiding potentially serious side effects.

Due to its extensive metabolism and its lack of appropriate functional groups which might be used to conjugate it to a protein carrier, the only generally useful method for the analysis of propranolol in body fluids is gas chromatography-mass spectrometry (GC-MS). Because the GC-MS method is both highly complex and expensive, it has not attained routine clinical use.

There have been published reports of radioimmunoassays for propranolol, but these assays suffer from unacceptably high cross reactivity with inactive propranolol metabolites frequently encountered in biological samples. This cross reactivity is the result of using the propranolol side chain nitrogen as the point of attachment to the protein carrier. The antibodies generated by these compounds recognize the ring end of the propranolol molecule which is common to many of the inactive metabolites.

Accordingly, it is a principal object of the present invention to provide new derivatives of propranolol which can be used to prepare antibodies to propranolol that recognize the side chain end of the propranolol molecule.

It is another object of the present invention to provide new derivatives of propranolol which can be conjugated to a tracer moiety for use in immunoassay applications.

It is a further object of the present invention to provide a highly sensitive and specific immunoassay of propranolol.

It is still a further object of the present invention to provide an immunoassay of propranolol which is significantly simpler and less expensive than the GC-MS method.

SUMMARY OF THE INVENTION

The problems of the prior art are overcome by the discovery of propranolol derivatives which allow covalent attachment of a protein carrier to their ring end, thus generating antibodies that recognize the side chain end of the propranolol molecule. Since the side chain end of the propranolol molecule is significantly altered in the inactive metabolites, the antibodies produced show negligible cross-reactivity to the inactive metabolites. Not only can these derivatives be used to prepare antiserum to propranolol for immunoassay applications, they can also be conjugated to a tracer moiety for immunoassay purposes.

The propranolol derivatives of the invention are aminoalkoxy derivatives. The preferred derivatives is 5'-(3 amino-1-propoxy) propranolol.

The process of the invention comprises the steps of conjugating an aminoalkoxy derivative of propranolol to a protein carrier, injecting the antigen into a host animal in order to produce antiserum, adding a known amount of tagged propranolol to a liquid sample containing an unknown amount of propranolol, adding the antiserum to the liquid sample and incubating the resulting mixture, separating the antibody-bound tagged propranolol and the antibody-free tagged propranolol, determining the amount of either the antibody-bound tagged propranolol or the antibody-free tagged propranolol, and comparing this determination with a standard.

If propranolol was present in the liquid sample, then the tagged and untagged propranolol would seek to attach themselves onto a finite number of antibody receptor sites and the amount of tagged propranolol which becomes bound is inversely proportional to the concentration of propranolol in the liquid sample. Similarly, the amount of antibody-free tagged propranolol will be a function of original propranolol concentration.

DESCRIPTION OF THE PREFERRED EMBODIMENT

Figure 1:
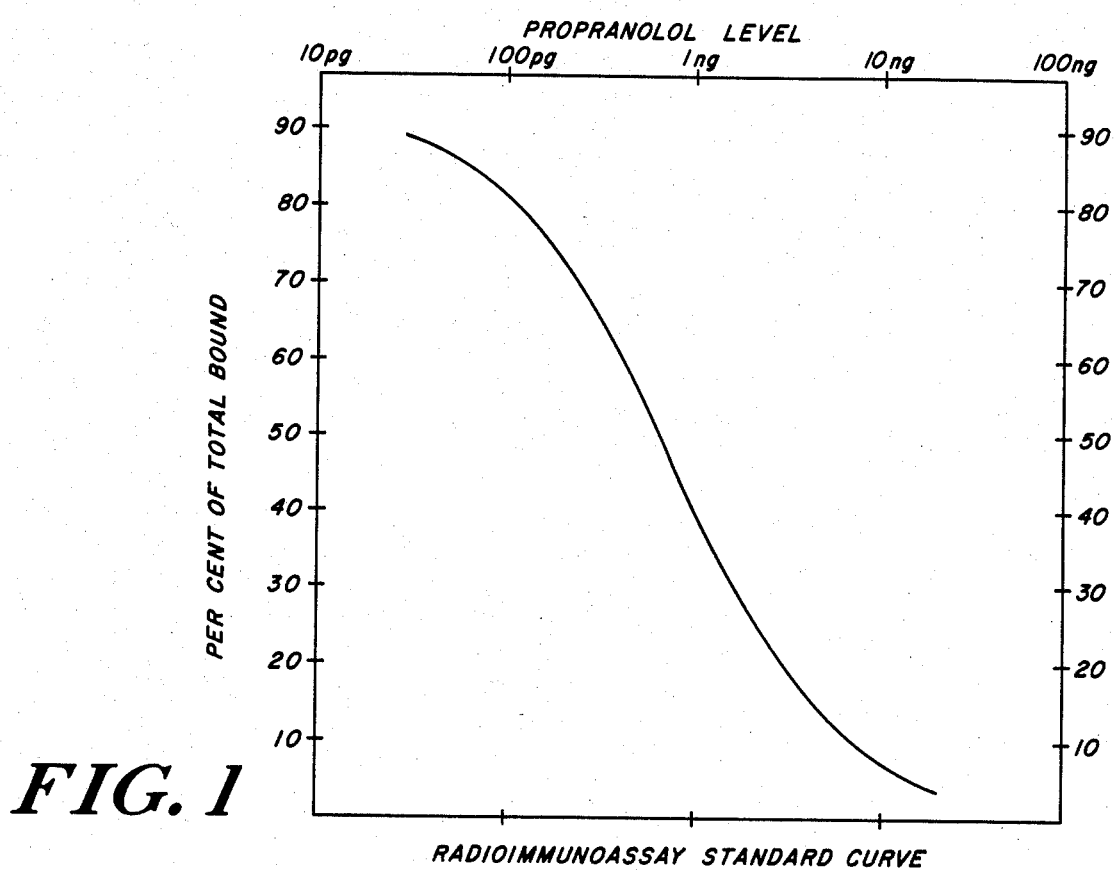
FIG. 1 is a standard curve for propranolol.

The propranolol derivatives of the present invention are aminoalkoxy derivatives having the structural formula

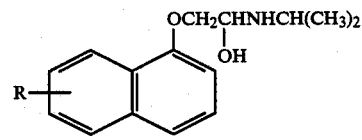

wherein R is $X-(CH_2)_n-O$, X is $NH_2$, n is 2,3,4, or 5, and R is attached in the 4',5',6',7' or 8' position. These derivatives can be used to prepare antiserum to propranolol for immunoassay applications. The derivatives can also be conjugated to a tracer moiety for use in immunoassays.

An immunoassay for propranolol utilizing the propranolol derivatives of the invention involves the following steps: preparing antigen by conjugating an aminoalkoxy propranolol derivative to a protein carrier via the amino group; producing antiserum to propranolol by injecting the antigen into a host animal, i.e., a rabbit; adding a known amount of tagged propranolol to a liquid sample containing an unknown amount of propranolol; adding the antiserum to the liquid sample and incubating the resulting mixture; separating the antibody-bound tagged propranolol and the antibody-free tagged propranolol; determining the amount of either the antibody-bound tagged propranolol or the antibody-free tagged propranolol; and comparing this determination with a standard.

In the immunoassay of the invention, the known amount of tagged propranolol can alternatively be added to the liquid sample at the same time as the antiserum or after incubation of the sample with the antiserum. If the known amount of tagged propranolol is added either before or at the same time the antiserum is added to the liquid sample, a competitive assay, then tagged and untagged propranolol molecules will be competing for the available antibody receptor sites. If the tagged propranolol is added after the antiserum is incubated with the liquid sample, a sequential assay, then tagged propranolol molecules will attach to the remaining receptor sites. The sequential method increases the sensitivity of the assay, but it requires one more step and takes a longer time than the competitive assay.

By preparing a series of samples with known propranolol concentrations and treating them in accordance with the immunoassay process of the invention, a standard curve of concentration of untagged propranolol vs. percent of total antibody-bound tagged propranolol can be prepared. Assays of samples with unknown propranolol concentrations will give a qualitative indication of the propranolol concentration if compared with such a curve.

The preferred propranolol derivatives of the invention are the 5'-(3-amino-1-propoxy) propranolol

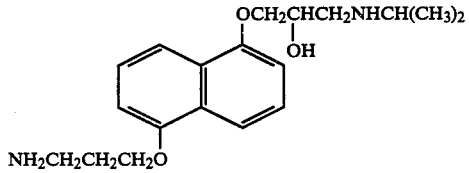

Conjugation of the propranolol derivatives of the invention to protein carriers via the 5' position of the propranolol molecule offers the best combination of good molecular orientation and synthetic feasibility.

Although the propranolol derivatives can be conjugated to any protein carrier, bovine serum albumin is the preferred macromolecule.

The aminoalkoxy propranolol derivatives of the invention can be tagged and used instead of tagged propranolol in the process of the invention. Regarding the nature of the tag, the state of the art is such that there are several types of tags available. Thus, the tagged propranolol or propranolol derivatives can contain a $^3H$, $^{131}I$, $^{14}C$, $^{125}I$ or other radioactive atom, an enzyme, an enzyme substrate, a fluorescent dye, or the like. The preferred tag is radioactive $^3H$.

The invention is further illustrated by the following non-limiting examples.

EXAMPLE 1

1-(2-Propylamino)-3-[5'-(3-amino-1-propoxy)-1'-naphthalenyloxy]-2-propanol was synthesized by the following steps:

A. To a solution of 24.0 g. of 1,5-dihydroxynaphthalene in 200 ml. of anhydrous DMF held under an atmosphere of nitrogen was added 3.6 g. of NaH (50% oil dispersion) in two portions to control foaming. The mixture was warmed to 90° C. after hydrogen evolution had subsided to complete salt formation, which is sluggish. The mixture was cooled and 20 g. of N-(3-bromopropyl) phthalimide was introduced in one portion and the reaction mixture heated to 100°-110° C. with stirring overnight. The solvent was subsequently distilled off at 1 mm and 60 C., and the viscous black residue treated with 400 ml. of chloroform to precipitate most of the unreacted 1,5-dihydroxynaphthalene. The filtrate was purified by silica gel column chromatography and recrystallized from ethanol, to afford 7.6 g. of 5'-(N-3-phthalimidyl-1-propoxy)-1'-naphthol, a pale yellow product (29%). M.P. 192°-194° C.

B. To a suspension of 7.6 g. of Dowex 1 strongly basic ion-exchange resin (OH form) in 100 ml. of epichlorohydrin was added 7.6 g. of 5'-(N-3-phthalimidyl-1-propoxy)-1'-naphthol, prepared in step A and the mixture was heated with stirring at 100° C. overnight. The resin was filtered off and the epichlorohydrin distilled at reduced pressure. The yellow solid residue was dried in vacuo to remove the last traces of epichlorohydrin. This crude product was further purified by elution through a short column of silica gel with dimethoxyethane. The solvent was evaporated and the solid residue was recrystallized from ethanol, affording 8.3 g. of the desired product (94%), 1'-(2,3-epoxypropoxy)-5'-(N-3-phthalimidyl-1-propoxy) naphthalene.

C. To a 100 ml. portion of anhydrous methylene chloride held under a nitrogen atmosphere and cooled to 0° C. was added 2 ml. of anhydrous isopropylamine and 16.9 ml. of trimethylaluminum (2M in toluene) solution. This mixture was stirred at room temp. for 60 minutes and cooled to 0° C. again, and then a solution of 8.3 g. of 1-(2,3-epoxypropoxy)-5'-(N-3-phthalimidyl-1-propoxy)naphthalene, prepared in step B, in 150 ml. of dry methylene chloride was added from an additional funnel at the rate of about 3 ml./min. When all of the epoxide had been added, the mixture was stirred at room temp. until the reaction was completed, about 2 days. The solution was then cooled to 0° C. and treated cautiously with a solution of 6.3 g. of NaOH in 100 ml. of distilled water. The resulting emulsion was filtered to remove aluminum oxide, then transferred to a separatory funnel and the organic layer separated and washed with 200 ml. of distilled water. The organic layer was dried over MgSO$_4$ and evaporated to yield 8.73 g. of crude product, which was purified by silica gel chromatography to yield 5.73 g. of an off-white solid. Recrystallization from ethyl acetate afforded 5.58 g. of the desired product (58%), 1-(2-propylamino)-3-[5'-(N-3-phthalimidyl-1-propoxy)-1-naphthalenyloxy]-2-propanol.

D. A 5.0 g. quantity of 1-(2-propylamino-)-3-[5'-(N-3-phthalimidyl-1-propoxy)-1-naphthalenyloxy]-2-propanol, prepared in step C, was dissolved in 100 ml.

of ethanol and 0.8 ml. of redistilled hydrazine hydrate (85%) was added. This solution was refluxed for 24 hours. The reaction mixture was cooled and evaporated to leave a white residue, which was dried in vacuo to remove traces of hydrazine. The dried residue was treated with distilled water, adjusted to pH 2, warmed to 90 C. for 15 minutes, then filtered. The filtrate was adjusted to pH 10 and extracted twice with chloroform. The combined chloroform extracts were dried over MgSO$_4$ and evaporated to an amber oil, which was recrystallized from cyclohexane to afford 2.90 g. (80%) of the desired product 1-(2-propylamino)-3-[5'-(3-amino-1-propoxy)-1'naphthalenyloxy]2-propanol.

Antigen was prepared by dissolving a 100 mg. portion of succinylated bovine serum albumin in 10 ml. of 0.1 M sodium phosphate buffer at pH 5.3. To this solution was added 60 mg. of 1-ethyl-3-(3-dimethylaminopropyl)-carbodiimide and the mixture was stirred for 10 minutes. After this interval, 50 mg. of 1-(2-propylamino)-3-[5'-(3-amino-1-propoxy)-1'-naphthalenyloxy]-2-propanol was added in 5 mg. portions, over a period of one hour, with stirring, and occasionally sonicated to aid solution. The mixture was permitted to stir for two hours more at room temp. and was subsequently dialyzed against 16 liters of distilled water at 4° C overnight. The water was changed twice at 24 hour intervals and the dialysate lyophilized to yield 83 mg. of conjugate.

Five New Zealand White rabbits were injected with an emulsion of the antigen as follows. For each animal, a solution was prepared consisting of 1 mg. of antigen dissolved in 0.8 ml. of 0.01M phosphate buffered saline at pH 7.4 and emulsified with 1.0 ml. of complete Freund's adjuvant. One hundred microliters of this emulsion was injected subcutaneously into each of the hind toe pads with the remainder divided between the hindquarters intramuscularly. One week later the animals were boosted with the same formulation, and additional boosts were administered at monthly intervals thereafter. All five animals had attained satisfactory titres after four months and five injections. Bleedings were taken from the central ear artery seven to ten days after each boost, and weekly once the titre was sufficient. Blood was allowed to clot overnight at 4° C. and centrifuged to separate antiserum.

For the assay of plasma samples containing unknown amounts of propranolol, the following procedure was employed. To suitably labelled glass vials with teflon-lined screw caps was added 100 microliters of each unknown plasma, one blank control plasma pool from drug-free volunteers, and the reference standard plasmas, made from the same blank pool by adding measured amounts of dl-propranolol to obtain between 25 and 500 ng/ml concentrations. Each sample was then treated with 20 microliters of 1.25M NaOH and 500 microliters of toluene and mechanically agitated for 15-20 minutes. The addition of NaOH prevents the extraction of 4-hydroxypropranolol into the toluene. The vials were centrifuged briefly to separate the layers, then duplicate 50 microliter aliquots were pipetted from each supernate into appropriately labelled silanized glass tubes and evaporated under nitrogen. Each tube was then treated with 300 microliters of assay buffer to redissolve the sample.

Radioactive dl-[4-$^3$H]-propranolol with a specific activity of 21 C/mMol was obtained from the Radiochemical Center Amersham. This tritiated propranolol was diluted in the assay buffer just prior to use to obtain about 15000 cpm in 100 microliters of solution; 100 microliters of this preparation was added to each tube, including two background controls. The propranolol antiserum was diluted to 1:2000 in the buffer and 100 microliters of this solution was added to each tube with the exception of the background controls. The tubes were then vortexed, incubated at 37° C. for one hour, and cooled in an ice bath for 10 minutes prior to the addition of dextran-coated charcoal suspension.

Each tube was treated with one ml. of cold dextran-coated charcoal suspension and vortexed briefly, then incubated at 0° C. for 7–10 minutes prior to centrifugation at 5000 RPM in a refrigerated centriguge for 25 minutes. The supernatants were decanted into suitably labelled scintillation vials, dissolved in 10 ml. of counting cocktail and counted for 1–5 minutes. Counting cocktail was prepared by dissolving 40 g. of Omnifluor TM (purchased from New England Nuclear) and 2 liters of S-A-S Solubilizer TM (purchased from Research Products International Corp.) in 10 liters of toluene.

The sensitivity of this immunoassay for dl-propranolol is indicated by the standard dose response curve shown in FIG. 1. Plasma samples containing propranolol concentrations from 30 pg./ml to 25 ng/ml could be reliably measured using the extraction procedure outlined above with 50 microliter aliquots of the plasma extract. The amount of extract can be increased up to 200 microliters in the same assay without the need to run a separate standard curve. Sensitivity can be further increased by extraction of a larger volume of plasma, but the reference plasma standards must be extracted in the same manner since recovery of propranolol may vary with a change in the relative volumes of plasma and solvent. The intra-assay precision of the immunoassay for dl-propranolol was 4% and the inter-assay precision was 5%.

EXAMPLE 2

The specificity of the antiserum produced in Example 1 is shown in Table 1. The data are presented to indicate the amount of the given compound required to produce 50% inhibition of $^3$H propranolol-antibody complex formation (ID50). This value is also expressed as a percentage indicating the relative efficiency of the compound with respect to propranolol as an inhibitor.

It is apparent that only the hydroxypropranolols cross react to any significant extent with the antiserum. Inhibition by side-chain metabolites is negligible. This is due to the fact that the antibodies generated by the novel propranolol derivatives recognize the side chain end of the propranolol molecule which is significantly altered in the inactive metabolites.

TABLE 1

| Compound | Structure | A ID$_{30}$ |
|---|---|---|
| Propranolol | 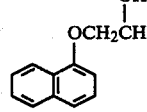 | 500 pg. (100%) |

TABLE 1-continued

| Compound | Structure | A ID$_{30}$ |
|---|---|---|
| 4-Hydroxy-Propranolol | OH / OCH$_2$CHCH$_2$NHCH(CH$_3$)$_2$ / naphthalene with OH | 1666 pg. (30%) |
| 5-Hydroxy-Propranolol | OH / OCH$_2$CHCH$_2$NHCH(CH$_3$)$_2$ / naphthalene with OH | 555 pg. (90%) |
| Propranolol Glucuromide | OCH$_2$CHCH$_2$NHCH(CH$_3$)$_2$ with glucuronide | 700 ng. (0.07%) |
| Propranolol Glycol | OCH$_2$CHCH$_2$OH / OH / naphthalene | no effect up to 70 micrograms |
| Naphthoxy Lactic Acid | OH / OCH$_2$CHCOOH / naphthalene | no effect up to 50 micrograms |
| N—desisopropyl Propranolol Amino | OH / OCH$_2$CHCH$_2$NH$_3$ / naphthalene | 780 ng. (0.06%) |

As seen by Table 1, the antiserum shows significant cross reactivity with the active 4-hydroxy metabolite. However, by using a simple toluene extraction step prior to assay, the contribution of the 4-OH metabolite can be excluded and the interfering substances eliminated. The antisera will also cross-react with 5-OH propranolol, but this metabolite is found only in rat urine.

EXAMPLE 3

Figure 2:
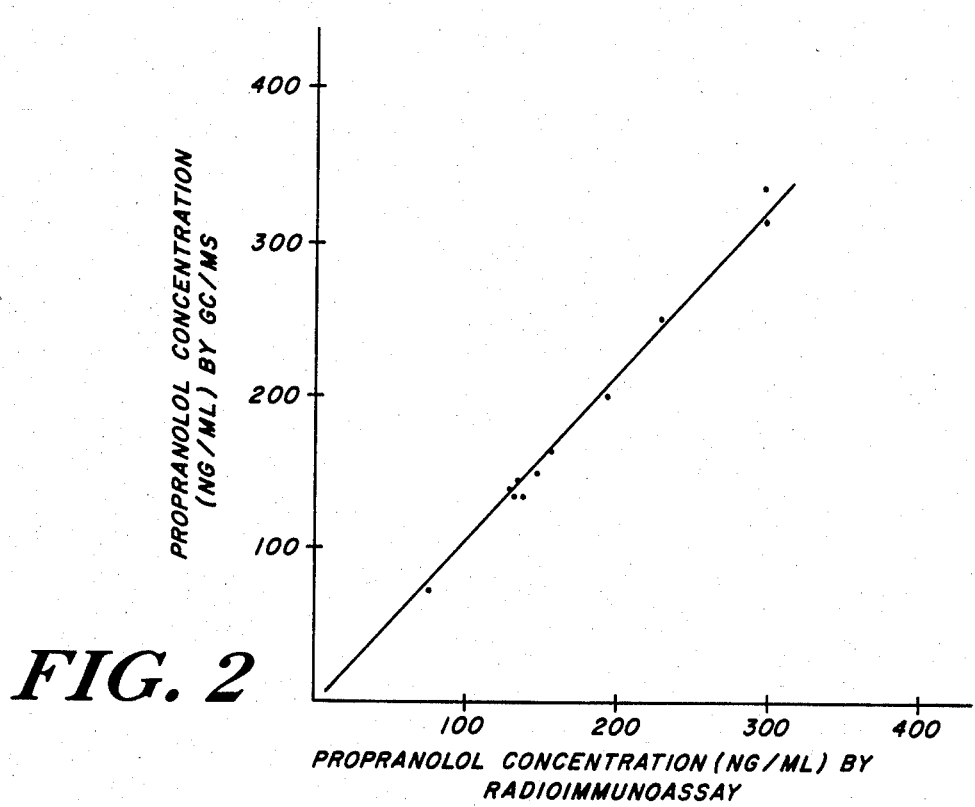
FIG. 2 is a graph illustrating the correlation between the GC/MS method and the immunoassay of the invention.
Figure 3:
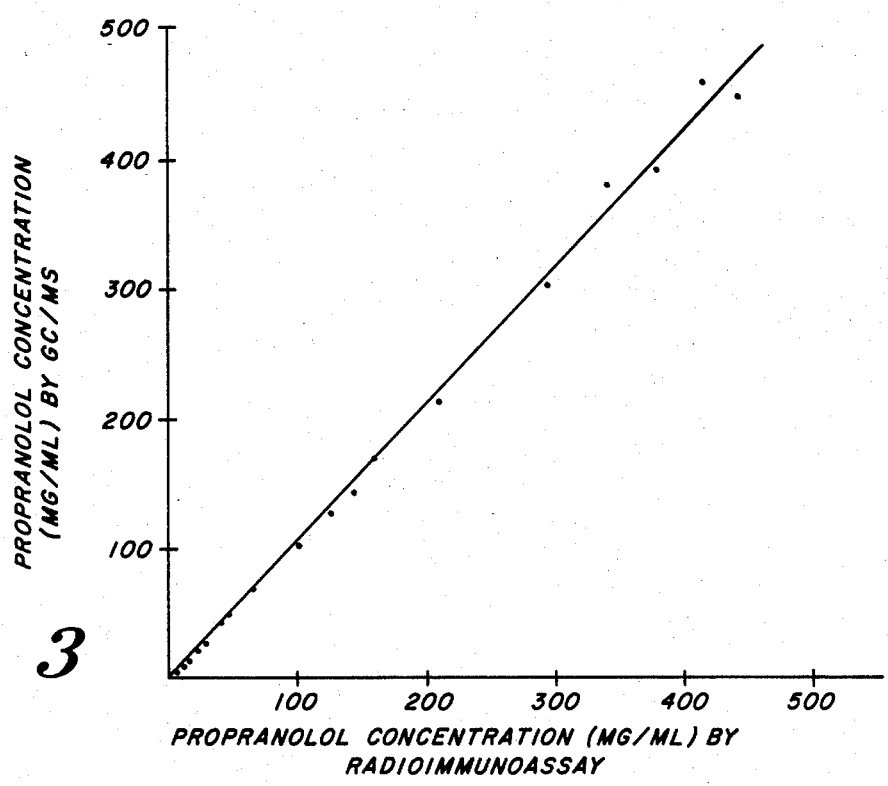
FIG. 3 is a graph illustrating the correlation between the GC/MS method and the immunoassay of the invention.

In order to assess the ability of the immunoassay to accurately measure propranolol levels in plasma samples, several experiments using human and dog plasmas which had been previously quantitated by GC/MS were performed according to the procedure of Example 1. FIG. 2 shows the correlation results for an experiment using plasma samples obtained from three human subjects maintained on a fixed oral dose of propranolol. The correlation coefficient for this experiment was 0.99. FIG. 3 shows the correlation results for an experiment using plasma samples obtained from two dogs at intervals between 5 minutes and 10 hours following a single I.V. dose of propranolol. The correlation coefficient for this experiment was 0.99.

EXAMPLE 4

5'-carboxymethoxy-propranolol can be prepared according to the following procedure. A quantity of 1,5-dihydroxynaphthalene is first alkylated with bromoacetonitrile and the monosubstituted product is then reacted with epichlorohydrin in the usual manner. The resulting epoxide intermediate is aminated with a complex of isopropylamine and trimethylaluminum to afford 5'-cyanomethoxy-propranolol, which is subsequently hydrolyzed with aqueous base to 5'-carboxymethoxy propranolol. The length of the side chain can be extended by choice of appropriate starting bromonitriles, and the position of the side chain on the ring can be varied by substitution of appropriate naphthalenediols.

While this invention has been described with reference to its preferred embodiment, other embodiments can achieve the same results. Variations and modifications of the present invention will be obvious to those skilled in the art and it is intended to cover in the appended claims all such modifications and equivalents as fall within the true spirit and scope of this invention.

We claim:

1. Propanolol derivatives selected from a group consisting of

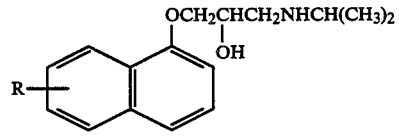

wherein
R is NH$_2$—(CH$_2$)$_n$—O;
n=2,3,4, or 5; and
R is attached in the 4',5',6',7' or 8' position.

2. 5'-(3-amino-1-propoxy) propranolol.

* * * * *